(12) United States Patent
Crocker et al.

(10) Patent No.: US 6,858,631 B1
(45) Date of Patent: Feb. 22, 2005

(54) POLYMORPHIC, AMORPHOUS AND HYDRATED FORMS OF 5-CHLORO-3-(4-METHANESULFONYLPHENYL)-6'-METHYL-[2,3']BIPYRIDINYL

(75) Inventors: Louis S. Crocker, Belle Mead, NJ (US); Dongwei Cai, Edison, NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 10/660,936

(22) Filed: Sep. 12, 2003

Related U.S. Application Data (60) Continuation of application No. 10/342,379, filed on Jan. 14, 2003, now abandoned, which is a continuation of application No. 10/180,399, filed on Jun. 26, 2002, now abandoned, which is a division of application No. 09/724,522, filed on Nov. 28, 2000, now Pat. No. 6,441,002.
(60) Provisional application No. 60/167,922, filed on Nov. 29, 1999.

(51) Int. Cl.[7] .................. A61K 31/44; C07D 401/02
(52) U.S. Cl. ............................. 514/334; 546/257
(58) Field of Search .................... 546/257; 514/334

(56) References Cited

U.S. PATENT DOCUMENTS

| | | | |
|---|---|---|---|
| 5,321,033 A | 6/1994 | Down et al. |
| 5,861,419 A | 1/1999 | Dube et al. |
| 6,040,319 A | 3/2000 | Corley et al. |
| 6,040,450 A | 3/2000 | Davies et al. |
| 6,127,545 A | 10/2000 | Pye et al. |
| 6,130,334 A | 10/2000 | Pye et al. |
| 6,204,387 B1 | 3/2001 | Davies et al. |
| 6,252,116 B1 | 6/2001 | Corley et al. |

FOREIGN PATENT DOCUMENTS

| | | |
|---|---|---|
| WO | WO 98/03484 | 1/1998 |
| WO | WO 99/55830 | 11/1999 |
| WO | WO 01/92230 | 12/2001 |
| WO | WO 02/096877 A1 | 5/2002 |

OTHER PUBLICATIONS

R.W. Friesen, et al., Bioorganic & Medicinal Chemistry Letters, (1998), vol. 8, No. 19, pp. 2777–2782.
Jean–Francois Marcoux, et al., J. Org. Chem., (2001), vol. 66, No. 12, pp. 4194–4199.
Ian W. Davies, et al., J. Org. Chem., (2000), vol. 65, No. 25, pp. 8415–8420.
Jean–Francois Marcoux et al., Organic Letters, (2000), vol. 2, No. 15, pp. 2339–2341.
Ian W. Davies, et al., J. Org. Chem., (2000), vol. 65, No. 15, pp. 4571–4574.
Biles, J.A., Journal of Pharmaceutical Sciences, vol. 51, No. 7, pp. 601–617, 1962.
Haleblian, et al., Journal of Pharmaceutical Sciences, vol. 58, No. 8, pp. 911–929, Aug. 1969.
Khoshkhoo, et al., Journal of Physics D., vol. 26, No. 8B, pp. B90–B93, Aug. 1993.

*Primary Examiner*—Zinna Northington Davis
(74) *Attorney, Agent, or Firm*—Raynard Yuro; David L. Rose (57) ABSTRACT

Polymorphic, amorphous and hydrated forms of the title compound having the following structure:

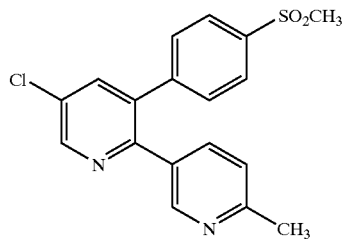

are disclosed. The compound is a potent and selective cyclooxygenase-2 (COX-2) inhibitor.

5 Claims, 8 Drawing Sheets

POLYMORPHIC, AMORPHOUS AND HYDRATED FORMS OF 5-CHLORO-3-(4-METHANESULFONYLPHENYL)-6'-METHYL-[2,3']BIPYRIDINYL

RELATED APPLICATIONS

This application is a continuation of application Ser. No. 10/342,379, filed on Jan. 14, 2003, now abandoned, which is a continuation of application Ser. No. 10/180,399, filed on Jun. 26, 2002, now abandoned, which is a division of application Ser. No. 09/724,522, filed on Nov. 28, 2000, now U.S. Pat. No. 6,441,002, which claims priority of Provisional Application No. 60/167,922, filed Nov. 29, 1999.

BACKGROUND OF THE INVENTION

The present invention relates to polymorphic, amorphous and hydrated forms of the title compound which has the chemical structure shown below:

Compound A

The compound is a potent and selective cyclooxygenase-2 (COX-2) inhibitor, useful primarily in the treatment of inflammation, pain and fever as well as other COX-2 mediated diseases, such as described in PCT Publication Nos. WO96/10012 and WO96/16934. Compound A is described in U.S. Pat. No. 5,861,419 granted on Jan. 19, 1999 (Example 23) incorporated by reference in its entirety.

Bipyridyl compounds generally are highly crystalline, poorly water soluble and hydrophobic, resulting in difficulties in the preparation of pharmaceutical formulations and problems associated with bioavailability. Accordingly, efforts were made to discover other forms of Compound A and to investigate the properties thereof. There were discovered three additional polymorphic forms, an amorphous form and two hydrates.

SUMMARY OF THE INVENTION

Polymorphic forms of Compound A, for purposes of this invention, are identified as Form I (onset of melting, m.p. 134–136° C., peak m.p. 138° C.), Form II (onset of melting, m.p.~131° C., peak m.p. 133° C.), Form III (onset of melting, m.p.~133° C., peak m.p. 135° C.) and Form IV (onset of melting, m.p.~134° C., peak m.p. 136° C.). Forms I through IV are anhydrous. An amorphous form and two hydrates have also been identified.

BRIEF DESCRIPTION OF THE DRAWINGS

The invention is described in connection with the appended drawings in which.

DETAILED DESCRIPTION

Polymorphic forms of Compound A, for purposes of this invention, are identified as Form I (onset of melting, m.p. 134–136° C., peak m.p. 138° C.), Form II (onset of melting, m.p.~131° C., peak m.p.~133° C.), Form III (onset of melting, m.p.~133° C., peak m.p. 135° C.) and Form IV (onset of melting, m.p.~134° C., peak m.p. 136° C.). Forms I through IV are anhydrous. An amorphous form and two hydrates have also been identified.

The polymorphs of the present invention are synthesized in accordance with the following examples which are illustrative.

PREPARATIVE EXAMPLE 1

The starting material compound A is made in accordance with Example 23 of U.S. Pat. No. 5,861,419 granted on Jan. 19, 1999.

EXAMPLE 1

Form II

Form II is obtained by crystallizing compound A obtained in accordance with Preparative Example 1 from ethyl acetate.

Differential Scanning Calorimetry showed an extrapolated onset of melting at 131±1° C., and a peak melting point of 132.5±0.1° C.

EXAMPLE 2

Form I

Form I was obtained by recrystallizing Form II obtained as described in Example 1 from a solvent mixture of isopropanol/hexane.

EXAMPLE 3

Form IV

Form IV appeared spontaneously in batches of compound A prepared as in Preparative Example 1.

Form IV is alternatively prepared by contacting Form I as described in Example 2 with an organic solvent, e.g., toluene and heptane, and then recrystallizing at a temperature less than 45° C., such as about 15° C.

Form IV is also alternatively prepared by dissolving Form II in an organic solvent, such as toluene and heptane, and then recrystallizing at a temperature less than 45° C., such as about 15° C.

EXAMPLE 4

Form III

Form III was prepared by stirring Form IV from Example 3 in water for 1 day, and then dehydrating at 90° C. in vacuo until Form III is present. The melting temperature onset was ca. 133° C. with an enthalpy of fusion of approximately 24 kJ/mol. The peak melting temperature was 135° C.

Alternatively, using the hemihydrate of Example 5, conducting a temperature XRPD of the hemihydrate at 130° C. resulted in the production of Form III.

EXAMPLE 5

Hemihydrate

The hemihydrate form of compound A is produced by stirring Form IV obtained in accordance with Example 3 in water for at least 1 day. XRPD analysis of the solid produced a diffractogramidentical to previous hemihydrate samples obtained for Form II. Thermogravimetry confirmed that Form IV had converted to the hemihydrate form, exhibiting a sharp weight loss of 2.45% on heating, which corresponds to a mole ratio of water to drug of 0.50%.

EXAMPLE 6

Sesquihydrate

The sesquihydrate of compound A is obtained by combining Form I in accordance with Example 2 and water (approximately 1.5 mol/mol compound).

EXAMPLE 7

Amorphous

The amorphous form of compound A is obtained by heating any polymorph to above its melting temperature (for example to 145° C.) under nitrogen, followed by quench cooling to room temperature under a dry atmosphere.

Characterization of Polymorphs

The polymorphic forms of compound A are characterized using the following procedures.

X-Ray Powder Diffraction Pattern Analysis

Polymorph 1 is crystalline by XRPD using a Scintag XDS-2000, Si(Li) Peltier-cooled solid state detector using a Cu K alpha source at 45 kV and 40 mA, and divergent beam (2 mm and 4 mm) and receiving beam slits (0.5 mm and 0.2 mm). Peak positions were calibrated using a standard silicon disk (97.5% pure).

Temperature XRPD studies were carried out under nitrogen, using a gold-plated copper stage with a Beryllium window on the cover. A Micristar temperature controller monitored and controlled the temperatures.

Temperature XRPD studies demonstrated that the compound did not undergo any transitions prior to melting, which was complete at 140° C., and that there was no conversion to a different polymorphic form. Similar results were obtained for Form II. The material remained amorphous and did not recrystallize.

Table 1 below lists the XRPD peak locations for Forms I, II, III and IV.

TABLE 1

X-ray Crystalline Reflections in °2 theta That Are Characteristic of Polymorphs I, II, III and IV using Cu K alpha

| Form I | Form II | Form III | Form IV |
|--------|---------|----------|---------|
| 7.1    | 5.6     |          | 5.7     |
| 9.7    | 9.4     | 10.5     |         |
| 11.8   | 10.7    | 16.1     |         |
| 15.5   | 17.6    |          | 15.2    |

TABLE 1-continued

X-ray Crystalline Reflections in °2 theta That Are Characteristic of Polymorphs I, II, III and IV using Cu K alpha

| Form I | Form II | Form III | Form IV |
|--------|---------|----------|---------|
| 20.1   |         |          | 17.1    |
|        |         |          | 19.5    |
| 22.7   |         | 22.4     | 21.7    |
| 24.1   |         |          | 23.5    |
|        |         |          | 23.6    |

Figure 5:
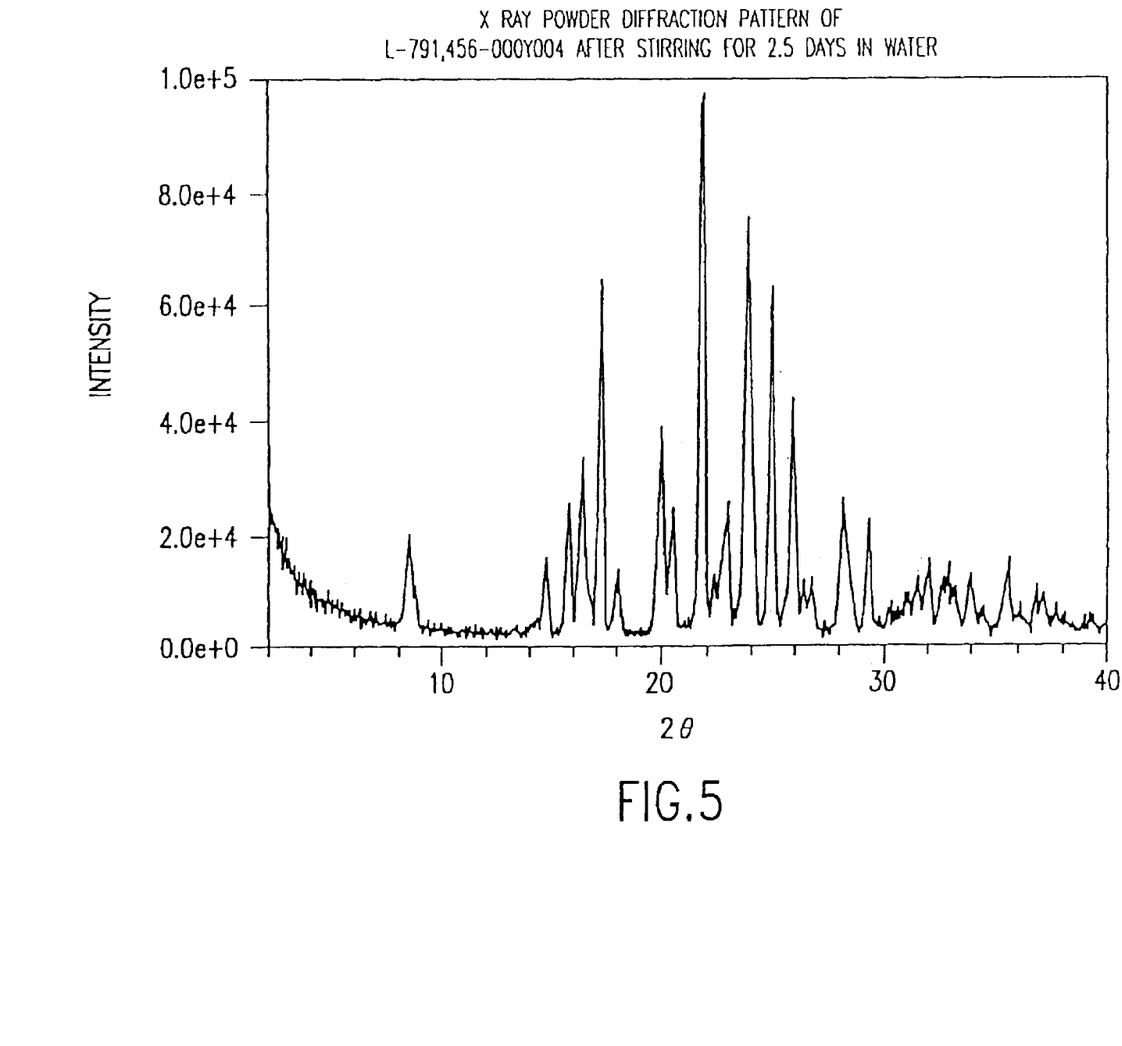
FIG. 5 is the XRPD pattern of the hemihydrate.
Figure 6:
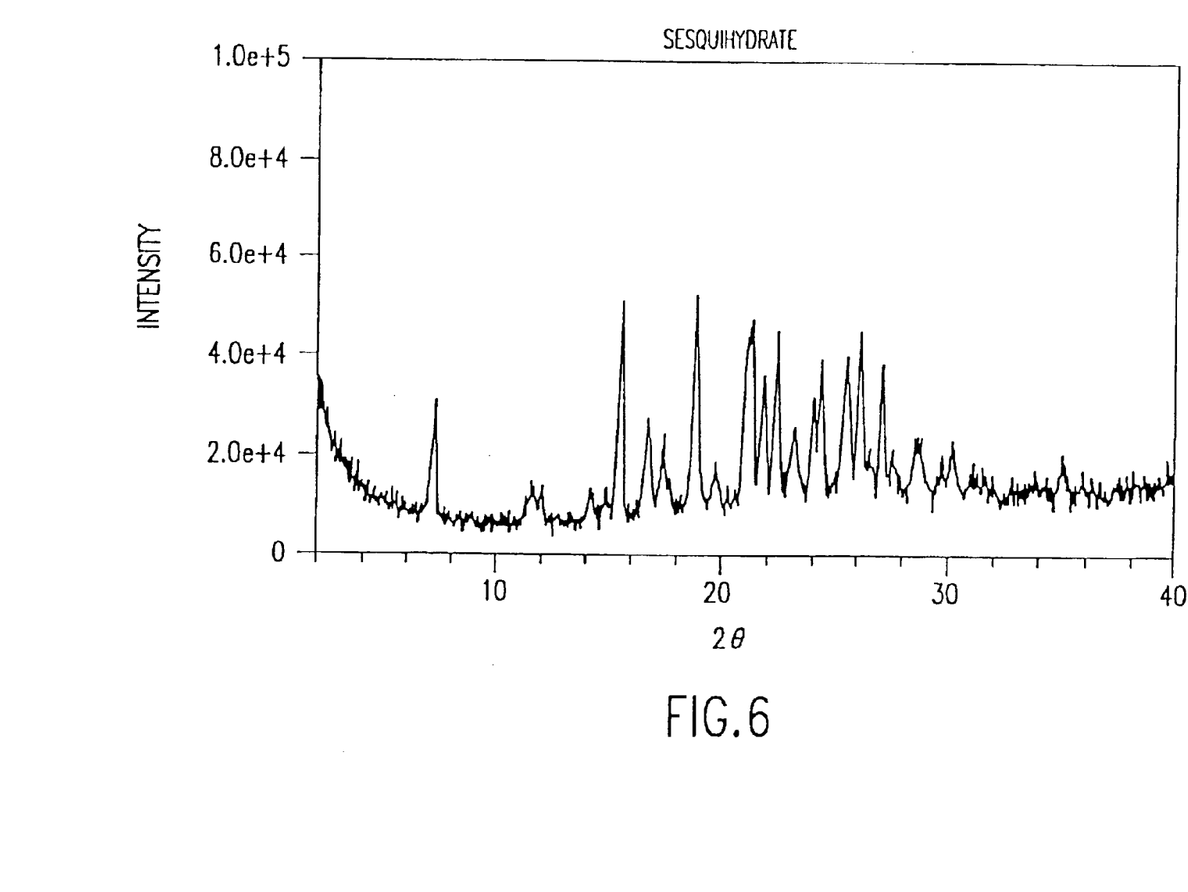
FIG. 6 is the XRPD pattern of the sesquihydrate.
Figure 7:
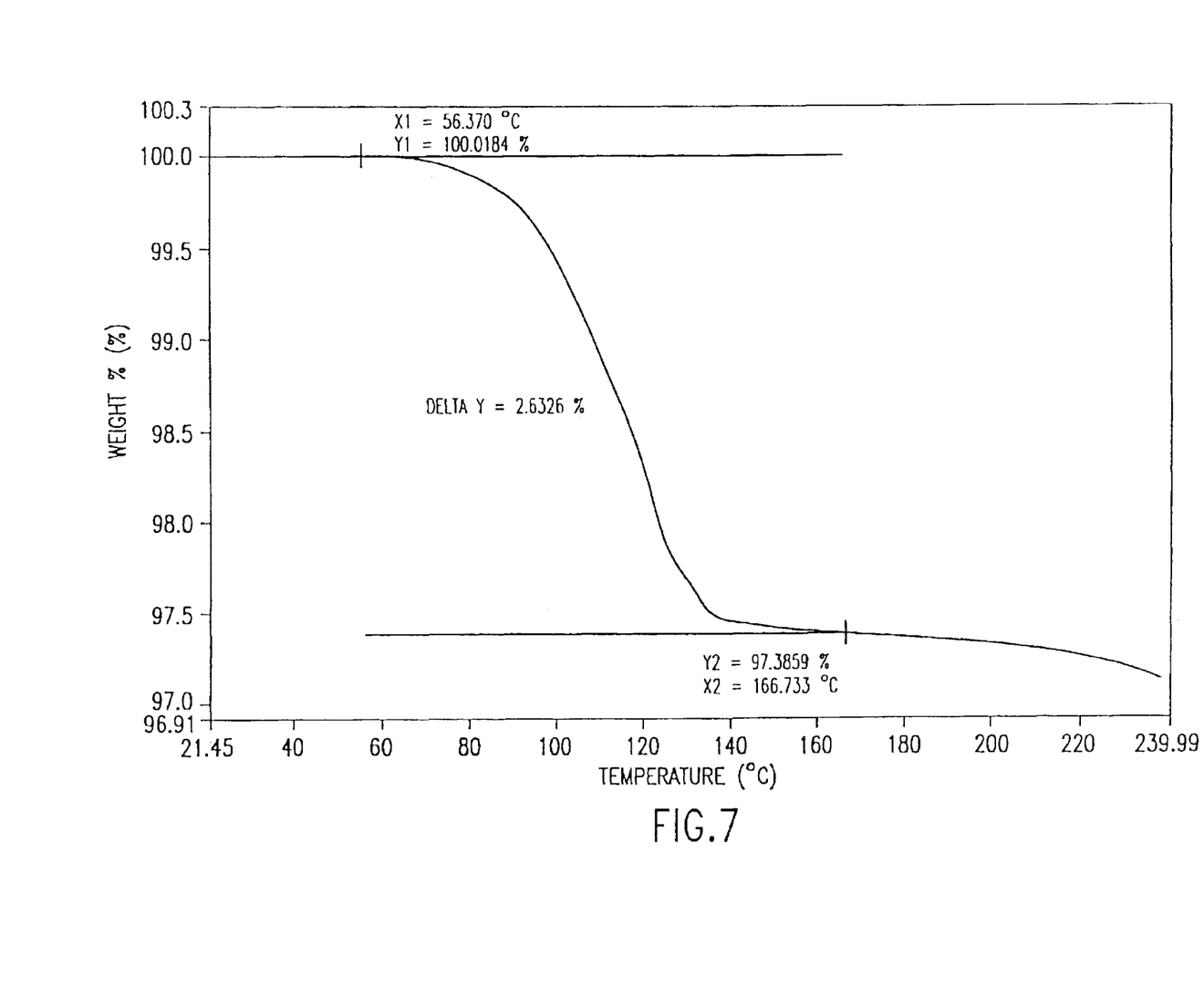
FIG. 7 is a thermogravimetric (TG) scan of the hemihydrate.
Figure 8:
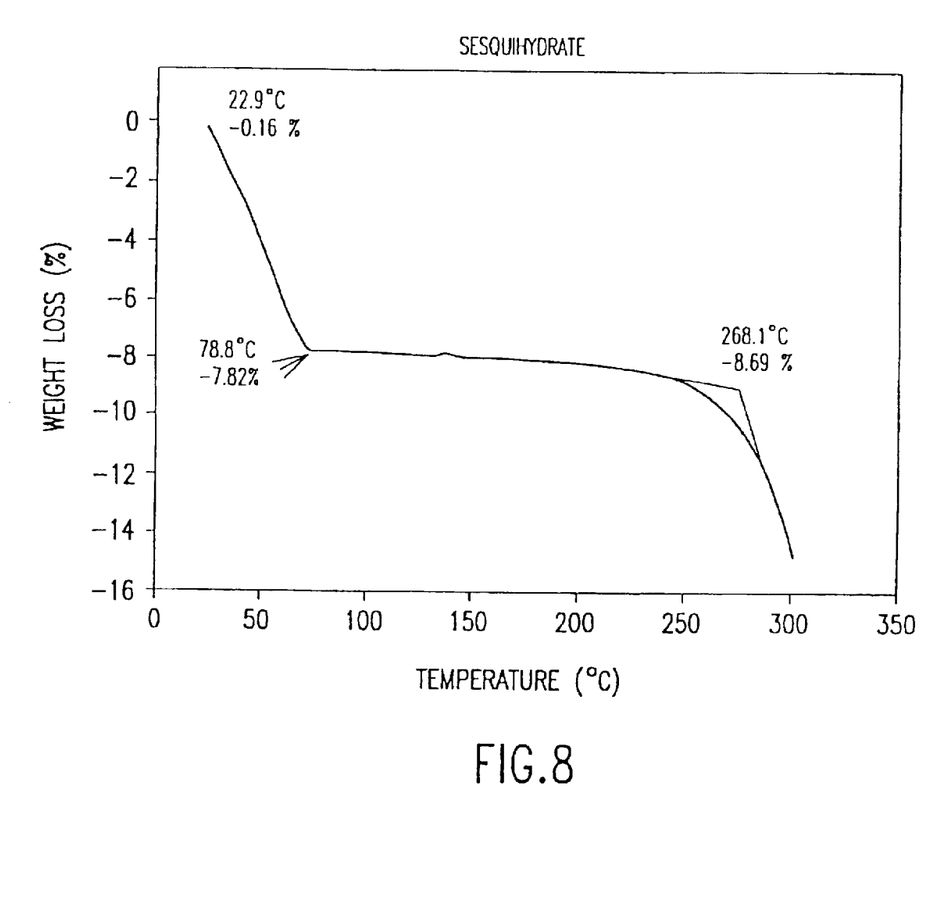
FIG. 8 is a TG scan of the sesquihydrate.

XRPD patterns for Forms I–IV are shown in FIGS. 1–4. XRPD patterns for the two hydrate forms are shown in FIGS. 5 and 6.

Differential Scanning Calorimetry (DSC)

Figure 1:
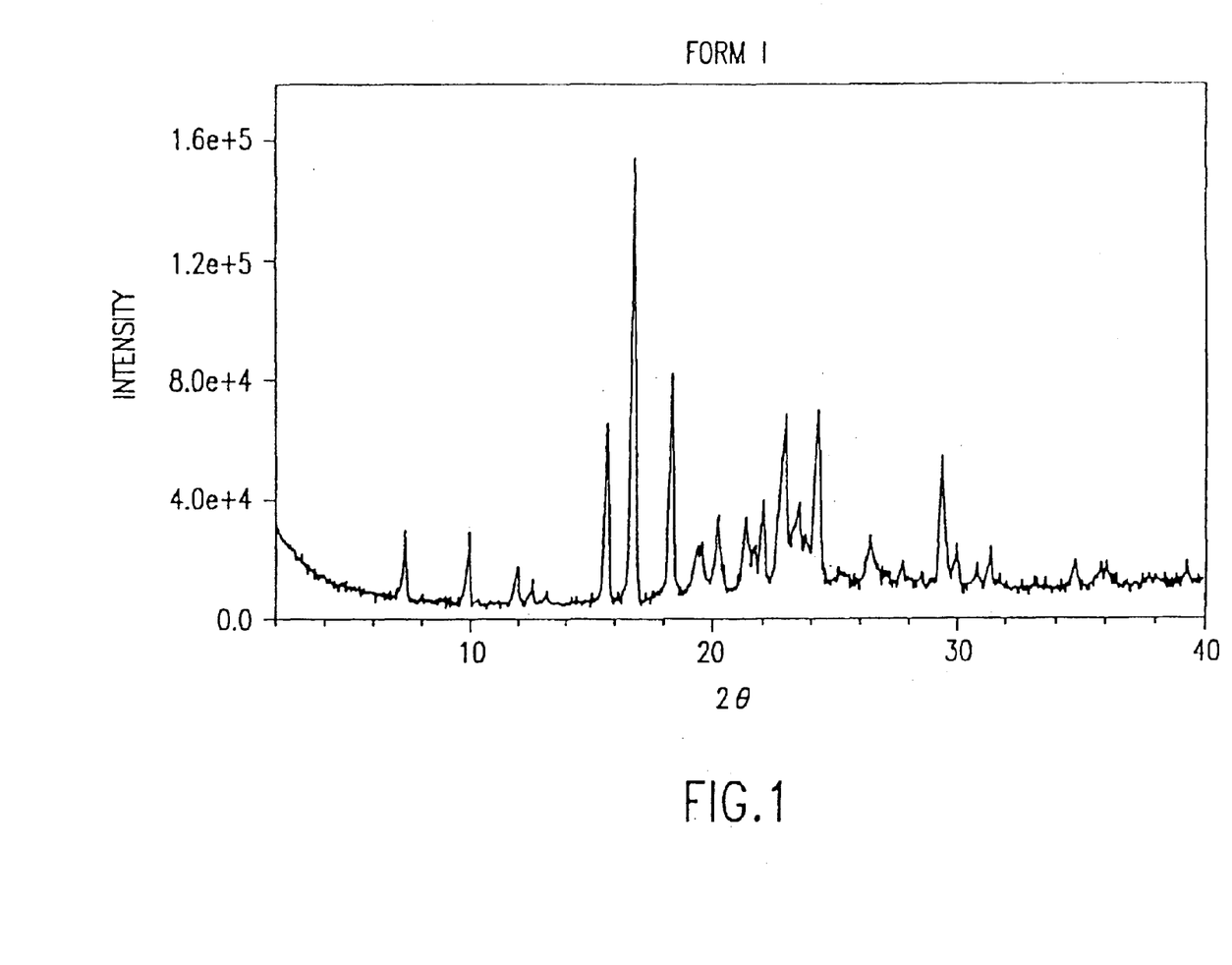
FIG. 1 is the X-ray powder diffraction (XRPD) pattern of Form I.
Figure 2:
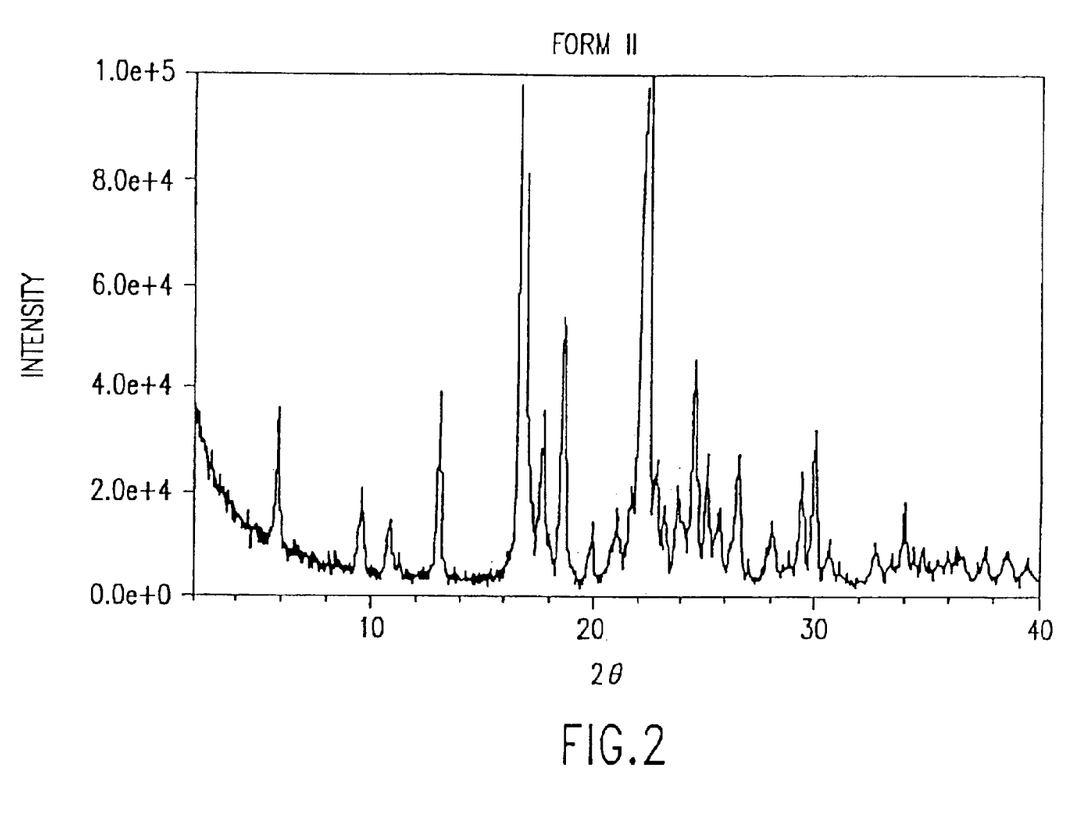
FIG. 2 is the XRPD pattern of Form II.
Figure 3:
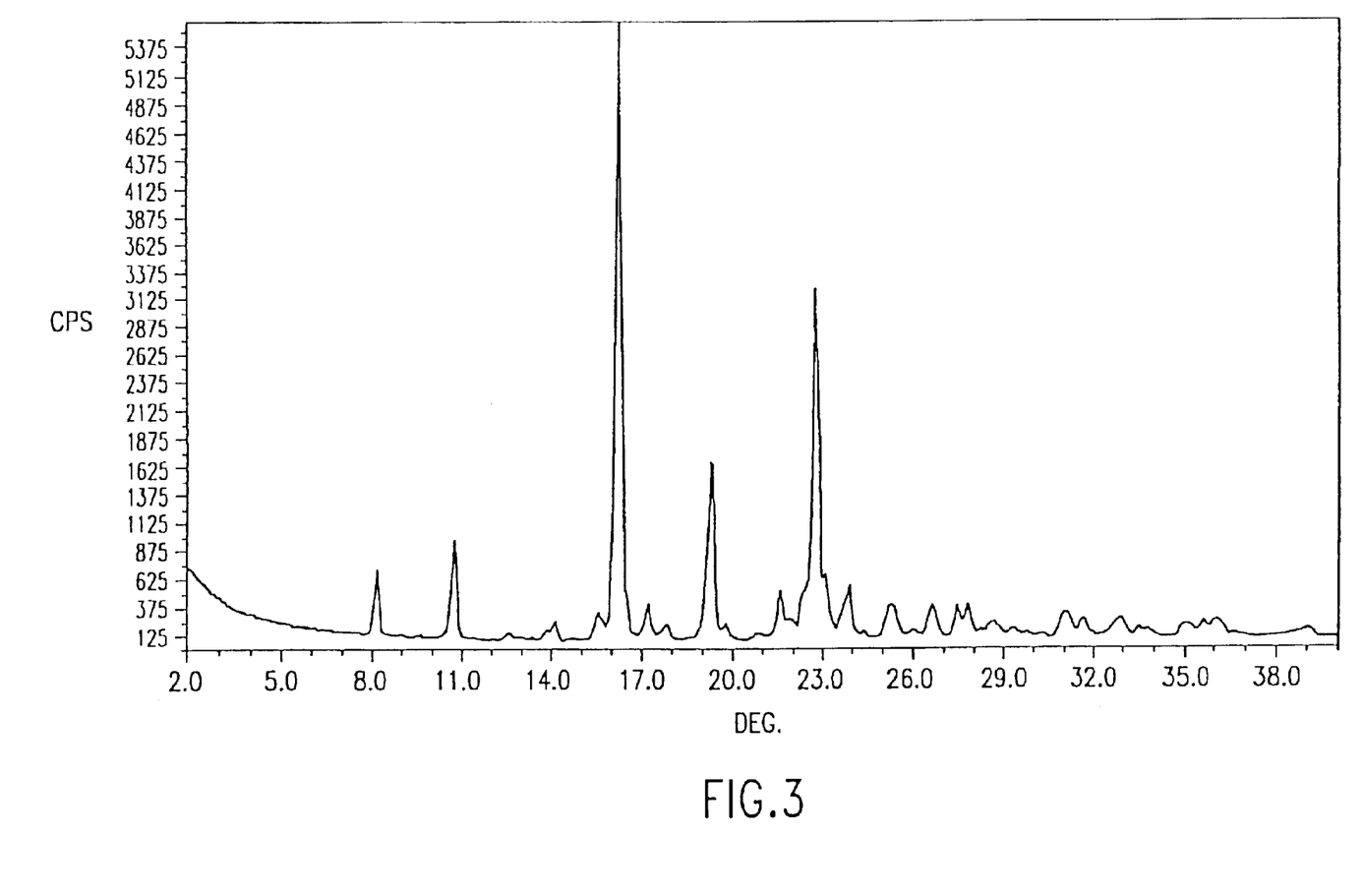
FIG. 3 is the XRPD pattern of Form III.
Figure 4:
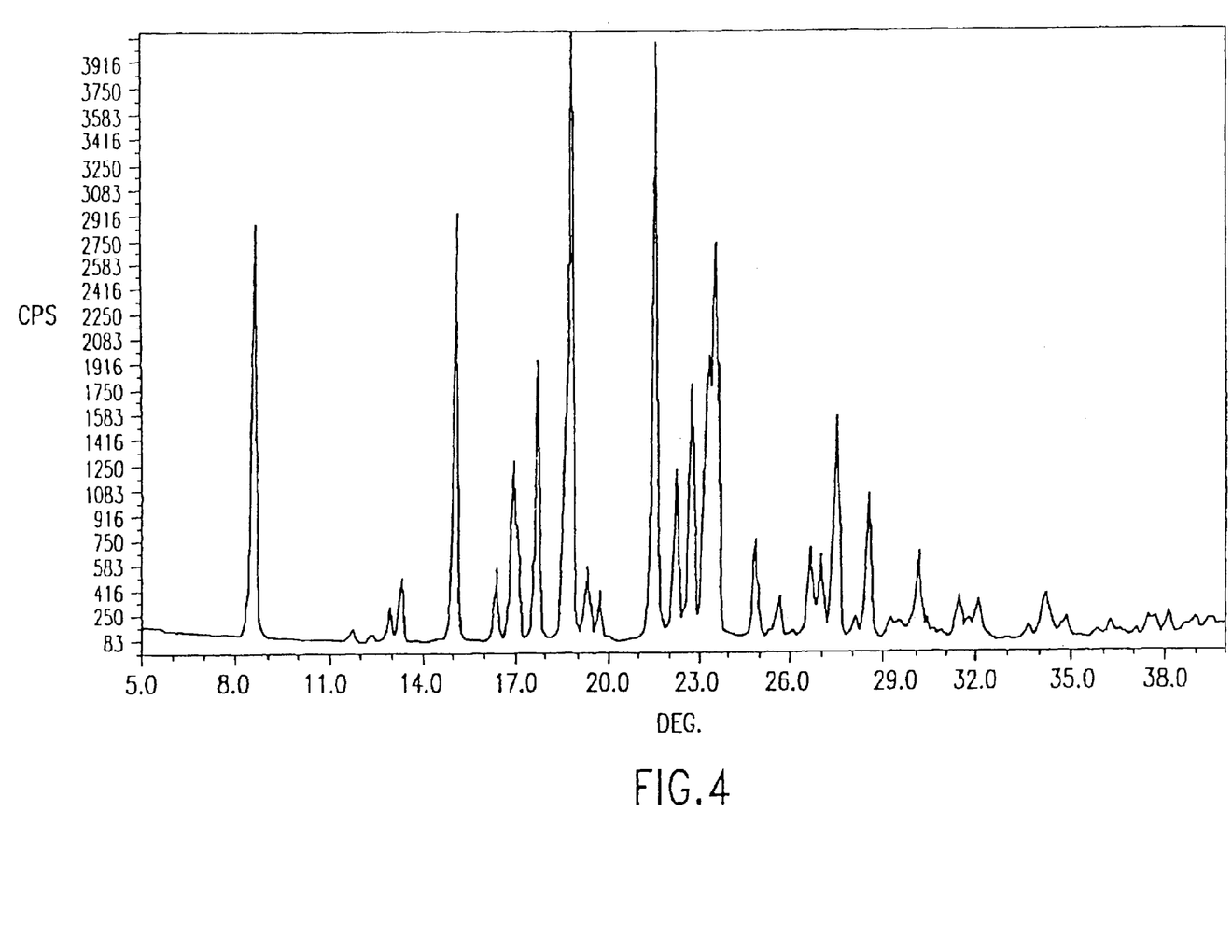
FIG. 4 is the XRPD pattern of Form IV.

The extrapolated melting temperature onset of Form I was 134.0±0.6° C. with an enthalpy of fusion of 27.2±0.9 kJ/mol at 10 deg/min under nitrogen in crimped aluminum pans (FIG. 1). The peak melting temperature was 138° C.

When measured using a TA Instruments DSC2910 instrument, at 10° C./min under a nitrogen atmosphere in an open aluminum pan, the onset of melting was 136° C. and the peak melting temperature was as described above. There were no significant changes with DSC scanning rate other than the expected shift in peak temperature. DSC thermal behaviour of Form I in crimped sample pans under nitrogen (60 mL/min) was measured using a Seiko robotic DSC (RDC-220) at 2, 10 and 20 deg/min. The DSC was calibrated for temperature and heat flow with gallium, indium and tin.

The melting temperature onset and enthalpy of fusion of Form I were slightly higher than those observed for Form II. These polymorphic forms do not recrystallize upon cooling from the melt nor do they recrystallize on reheating. The glass transition temperature of the amorphous form (midpoint, 10K/min, crimped aluminum pan) is 55° C.

Table 2 provides a comparison of the extrapolated melting temperature onset, $T_o$, and the enthalpy of fusion, $\Delta H$, for Forms I, II, III and IV.

TABLE 2

Extrapolated melting temperature onset, $T_o$, and Enthalpy of Fusion obtained by DSC at 10K/min in crimped pans under nitrogen

| Polymorphic form | $T_o$ (° C.) | Enthalpy of fusion, kJ/mol |
|------------------|--------------|----------------------------|
| Form I           | 134.0 ± 0.6  | 27.2 ± 0.9                 |
| Form II          | 131 ± 1      | 25.8 ± 0.2                 |
| Form III         | 133          | 22.7                       |
| Form IV          | 134.0 ± 0.1  | 27.9 ± 0.2                 |

The DSC thermogram for Form IV, obtained at a scanning rate of 10° C./min under nitrogen in crimped aluminum pans, consisted of a single symmetrical endotherm with a mean onset melting point of 134.0±0.1° C. and a heat of fusion of 27.9 kJ/mol. A scanning rate of 2° C./min confirmed that the observed endotherm was due to a single endothermic transition. The enthalpy of fusion of the different polymorphs are also similar.

Forms I and IV have similar solubilities. Form IV is slightly less soluble and slightly more stable at temperatures below 45° C. Forms I and IV are enantiotropic with Form IV converting to Form I at temperatures greater than 45° C. when in contact with organic solvents.

What is claimed is:

1. A polymorph of the compound of formula A:

which is Form I.

2. The polymorph in accordance with claim 1 wherein the polymorph has an x-ray powder diffraction pattern peak position, Cu K alpha, at about 9.7 degrees 2-theta.

3. The polymorph in accordance with claim 2 wherein the polymorph has at least one additional x-ray powder diffraction pattern peak position, Cu K alpha, at about 7.1, 11.8, 15.5 20.1, 22.7 and 24.1 degrees 2-theta.

4. A pharmaceutical composition comprised of a Form I polymorph of Compound A in accordance with claim 1 in combination with a pharmaceutically acceptable carrier.

5. The pharmaceutical composition in accordance with claim 4 wherein the form I polymorph has the physical characteristics described in the following table:

| Form | I |
|---|---|
| XRPD (peak positions, Cu K alpa) | 7.1 |
|  | 9.7 |
|  | 11.8 |
|  | 15.5 |
|  | 20.1 |
|  | 22.7 |
|  | 24.1 |

* * * * *